United States Patent
Dunlay et al.

(10) Patent No.: US 11,111,031 B1
(45) Date of Patent: Sep. 7, 2021

(54) FLIGHT CONTROL MANAGEMENT USING TOUCHSCREEN INTERFACES

(71) Applicant: Rockwell Collins, Inc., Cedar Rapids, IA (US)

(72) Inventors: Angela N. Dunlay, Marion, IA (US); Steven L. Kamada, Cedar Rapids, IA (US); Phillip J. Hamm, Cedar Rapids, IA (US)

(73) Assignee: Rockwell Collins, Inc., Cedar Rapids, IA (US)

(*) Notice: Subject to any disclaimer, the term of this patent is extended or adjusted under 35 U.S.C. 154(b) by 39 days.

(21) Appl. No.: 16/592,256

(22) Filed: Oct. 3, 2019

Related U.S. Application Data

(60) Provisional application No. 62/767,349, filed on Nov. 14, 2018.

(51) Int. Cl.
| | |
|---|---|
| *B64D 43/00* | (2006.01) |
| *G06F 3/0488* | (2013.01) |
| *G06T 11/00* | (2006.01) |
| *G06F 3/0481* | (2013.01) |
| *G06F 3/0482* | (2013.01) |
| *B64D 37/00* | (2006.01) |
| *G06T 13/80* | (2011.01) |

(52) U.S. Cl.
CPC .......... *B64D 43/00* (2013.01); *B64D 37/005* (2013.01); *G06F 3/0482* (2013.01); *G06F 3/0488* (2013.01); *G06F 3/04817* (2013.01); *G06T 11/001* (2013.01); *G06T 13/80* (2013.01); *G06T 2200/24* (2013.01)

(58) Field of Classification Search
CPC ... B64D 43/00; B64D 37/005; G06F 3/04817; G06F 3/0482; G06F 3/0488; G06T 11/001; G06T 13/80
USPC .......................................................... 701/3
See application file for complete search history.

(56) References Cited

U.S. PATENT DOCUMENTS

| | | | | |
|---|---|---|---|---|
| 3,942,364 | A * | 3/1976 | Bunker | G01L 3/26 73/114.13 |
| 9,772,712 | B2 | 9/2017 | Kneuper et al. | |
| 2005/0051666 | A1* | 3/2005 | Lee | B64C 30/00 244/10 |
| 2009/0306839 | A1* | 12/2009 | Youngquist | G01K 15/00 701/14 |
| 2015/0217856 | A1* | 8/2015 | Mesguen | B64C 19/00 701/3 |

(Continued)

*Primary Examiner* — William D Titcomb
(74) *Attorney, Agent, or Firm* — Suiter Swantz pc llo

(57) ABSTRACT

A touchscreen fuel panel. In embodiments, the fuel panel includes a touchscreen display and a controller coupled to the touchscreen display. The controller is configured to generate a graphical user interface at the touchscreen display and receive user inputs via the touchscreen display. In embodiments, the graphical user interface includes a pump menu with at least one selectable icon for a set of engine boost pumps and a plurality of individually selectable icons for forward, center, and aft pumps. The controller is configured to receive a user input representing a user interaction with the graphical user interface (e.g., an icon selection) via the touchscreen display. The controller is further configured to generate one or more control signals for the set of engine boost pumps, at least one forward pump, at least one center pump, or at least one aft pump based on the user input.

11 Claims, 5 Drawing Sheets

(56) References Cited

U.S. PATENT DOCUMENTS

| | | | | |
|---|---|---|---|---|
| 2015/0217857 A1* | 8/2015 | Mesguen | ............... | B64D 43/00 |
| | | | | 701/3 |
| 2015/0217874 A1* | 8/2015 | Mesguen | ............... | B64D 43/00 |
| | | | | 701/29.1 |
| 2017/0283083 A1* | 10/2017 | Behbahani-Pour | ...... | A62C 3/08 |
| 2018/0162546 A1* | 6/2018 | Gowda | ..................... | G06F 3/14 |
| 2018/0292953 A1* | 10/2018 | Pandya | ................. | B64D 43/00 |
| 2018/0348280 A1* | 12/2018 | Collins | ................ | G08B 21/185 |
| 2018/0354610 A1* | 12/2018 | Kneuper | ................ | B64C 17/10 |

* cited by examiner

FLIGHT CONTROL MANAGEMENT USING TOUCHSCREEN INTERFACES

PRIORITY

The present application claims the benefit under 35 U.S.C. § 119(e) of U.S. Provisional App. No. 62/767,397 (filed Nov. 14, 2018), which is incorporated herein by reference.

GOVERNMENT LICENSE RIGHTS

The U.S. Government has a paid-up license in this invention and the right in limited circumstances to require the patent owner to license others on reasonable terms as provided by the terms of FA8105-11-D-0001 awarded by the United States Air Force.

BACKGROUND

Currently employed flight control panels located in the cockpit rely on hard switches and digital readouts to manage and monitor the aircraft. This requires flight crew to manually perform several control operations and critical calculations. Improved control panels are needed in order to reduce human error, relieve flight crew of tasks that can be handled automatically, and provide flight crew with better access to information.

SUMMARY

In an aspect, embodiments of the inventive concepts disclosed herein are directed to a fuel management interface for a touchscreen control panel in the cockpit, such as a fuel panel. In embodiments, the fuel panel includes a touchscreen display and a controller coupled to the touchscreen display. The controller is configured to generate a graphical user interface at the touchscreen display and receive user inputs via the touchscreen display. In embodiments, the graphical user interface includes a pump menu with at least one selectable icon for a set of engine boost pumps and a plurality of individually selectable icons for forward, center, and aft pumps. The controller is configured to receive a user input representing a user interaction with the graphical user interface (e.g., an icon selection) via the touchscreen display. The controller is further configured to generate one or more control signals for the set of engine boost pumps, at least one forward pump, at least one center pump, or at least one aft pump based on the user input.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
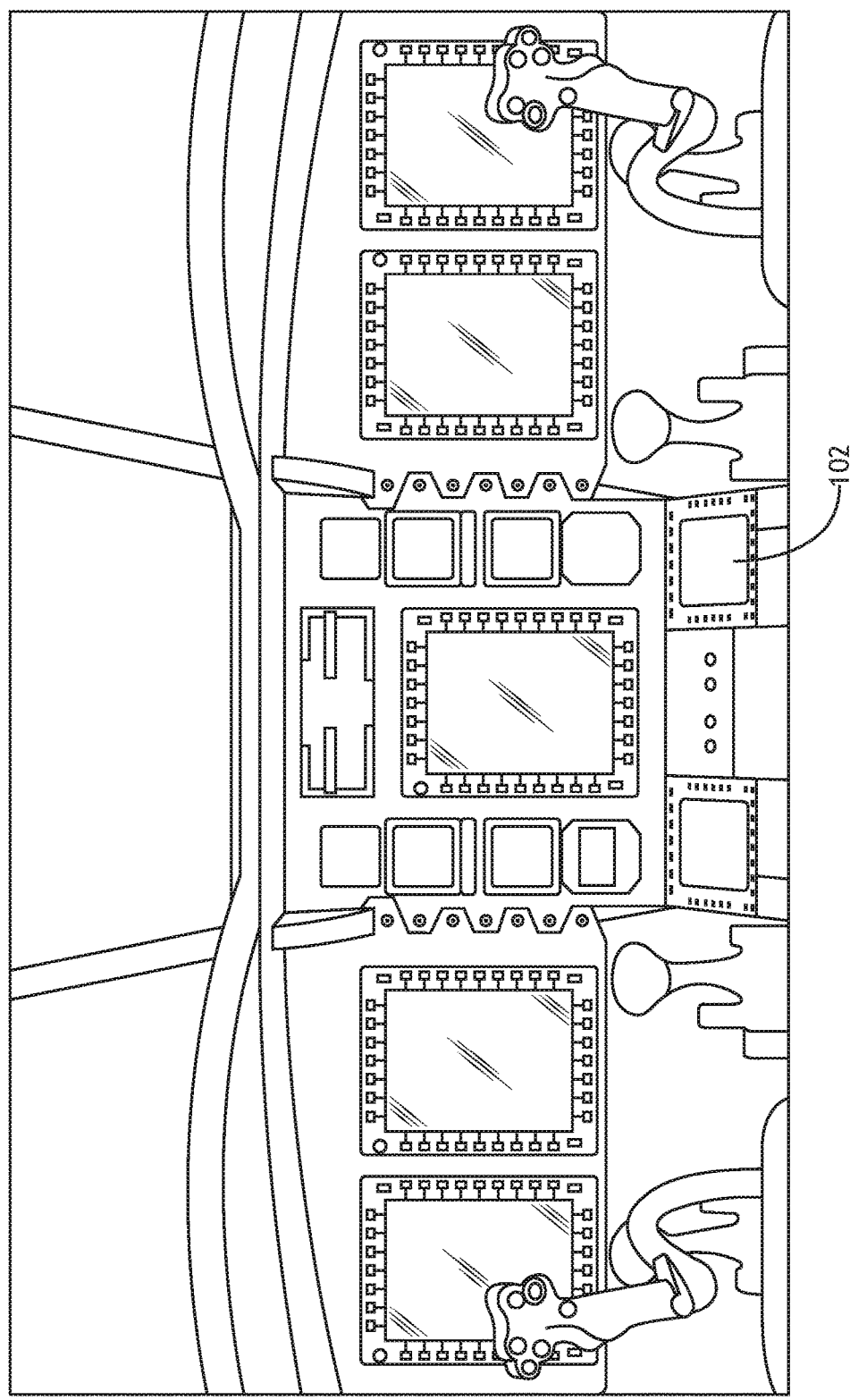
FIG. 1 shows an environmental view of an aircraft cockpit including an exemplary embodiment of a touchscreen fuel panel.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1 b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a touchscreen fuel panel that enables checklist automation. In embodiments, the fuel panel includes a touchscreen display and a controller coupled to the touchscreen display. The controller is configured to generate a graphical user interface at the touchscreen display and receive user inputs via the touchscreen display. The controller is further configured to execute an automated set of fuel management checklist procedures in response to a user input. In some embodiments, the controller can be alternatively or additionally configured to execute other automated sets of checklist procedures, for example, pre-flight, in-flight, taxi/takeoff/landing (TTL), and/or post-flight procedures.

Referring to FIG. 1, an environmental view of an aircraft cockpit 100 including an exemplary embodiment of a fuel management interface for a touchscreen fuel panel 102 that enables checklist automation. Existing aircraft environments include hard switches (e.g., toggles, knobs, flip switches, slide switches, etc.) for managing fuel in the aircraft. A touchscreen fuel panel 102 replaces existing hard switches, and is integrated within the center console or elsewhere in the aircraft environment so that it is conveniently accessible to flight crew.

Figure 2:
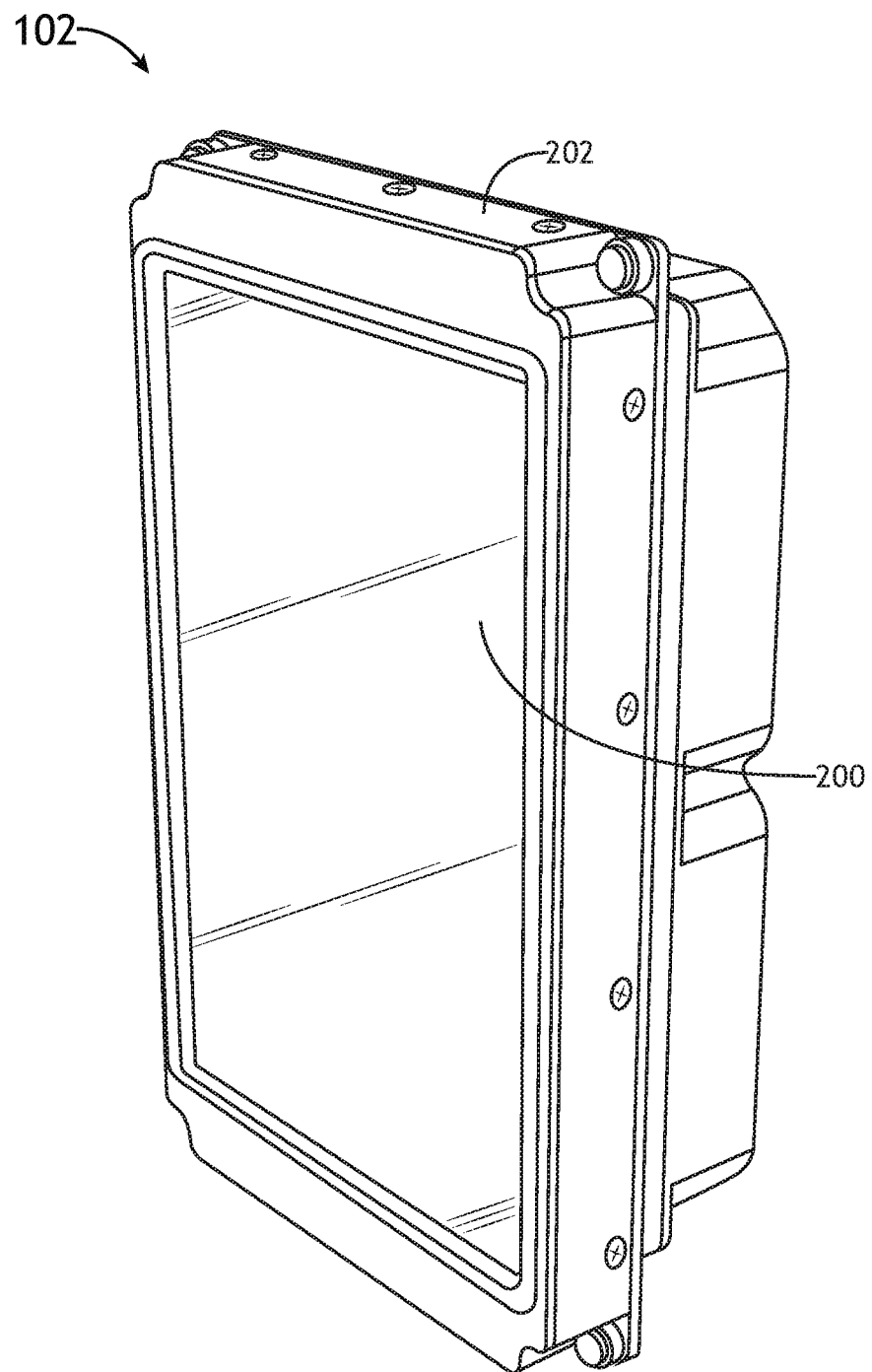
FIG. 2 shows a perspective view of a touchscreen fuel panel according to an exemplary embodiment.

Referring to FIG. 2, a perspective view of a touchscreen fuel panel 102 according to an exemplary embodiment is shown. The touchscreen fuel panel 102 is a self-contained device in data communication with other on-board avionics systems to receive and display data on a touchscreen display 200. The touchscreen display 200 allows users to interact with the connected systems, including through the execution of stored procedures. In at least one embodiment, the touchscreen display 200 employs glass resistive touch that may be glove compatible. The touchscreen fuel panel 102 includes an enclosure 202 that holds, carries, and/or is coupled to various electronic components of the touchscreen fuel panel 102. For example, the enclosure 202 can hold, carry, and/or be coupled with a touchscreen display 200, a controller or processor, memory, and one or more communication interface ports.

In at least one embodiment, a fuel management system including a touchscreen fuel panel 102 is conduction cooled. The system may employ AFD-3200 device architecture, include a NVIS Filter, support D-Zus rail installation, and/or support DAL A functionality. The touchscreen fuel panel 102 may meet DO-160G qualification and comply with DO-254 artifacts. The fuel management system may support DO-178 platform software, ARINC 661 display graphics rendering, ARINC 661 toolkit, and/or local and remote A661 graphics.

Figure 3:
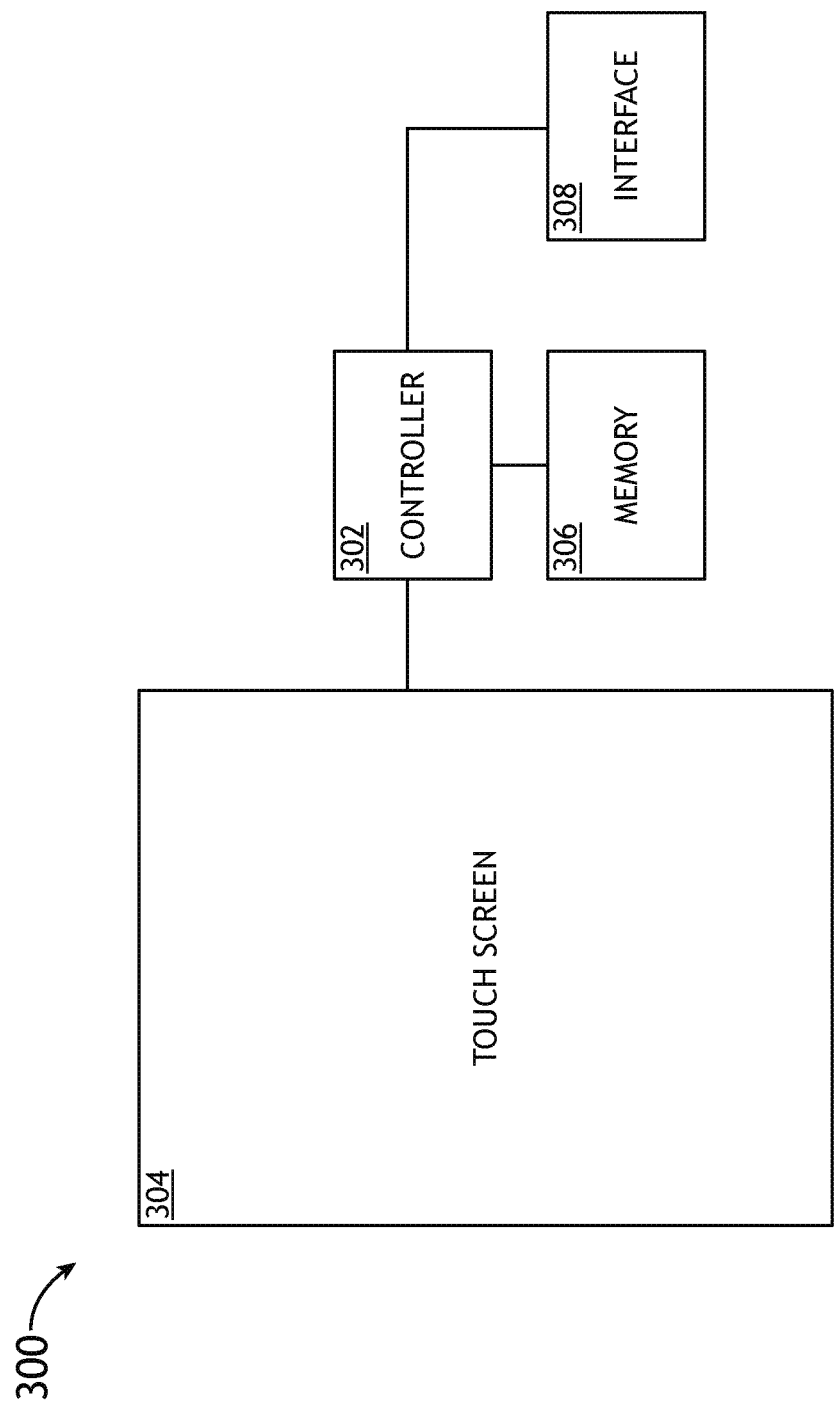
FIG. 3 shows a block diagram of a system for implementing a touchscreen fuel panel according to an example embodiment.

Referring to FIG. 3, a block diagram of a system 300 for implementing a touchscreen fuel panel according to an example embodiment is shown. The system 300 includes a controller 302 in data communication with a touchscreen 304 and a memory 306 for storing processor executable code. The controller 302 populates the touchscreen 304 with a graphical depiction of an aircraft fuel system.

In at least one embodiment, the system 300 includes an interface device 308 in data communication with the controller 302; such interface device 308 may comprise Ethernet, ARINC-429, RS-232, or other similar protocols. The interface device 308 allows the controller 302 to interact with avionics systems to retrieve real-time data for display and send instructions to those avionics systems. Furthermore, the controller 302 may query the avionics systems via the interface device 308 to determine an architecture of the fuel system (numbers of tanks, pumps, valves, etc.). The controller 302 may then create a graphical representation of the fuel system as it actually exists. The controller 302 may also query the avionics systems to determine acceptable status boundaries for the depicted systems and store those status boundaries in the memory 306.

The controller 302 provides processing functionality for at least the touchscreen fuel panel 300 and can include any number of processors, micro-controllers, circuitry, field programmable gate array (FPGA) or other processing systems. In at least one embodiment, the controller 302 is in data communication with a data storage element for storing checklist procedures and checklist results when such procedures are executed. The controller 302 can execute one or more software programs embodied in a non-transitory computer readable medium (e.g., memory 306) that implement techniques described herein. The controller 302 is not limited by the materials from which it is formed or the processing mechanisms employed therein and, as such, can be implemented via semiconductor(s) and/or transistors (e.g., using electronic integrated circuit (IC) components), and so forth.

The memory 306 can be an example of tangible, computer-readable storage medium that provides storage functionality to store various data and/or program code associated with operation of the controller 302 and touchscreen 304, such as software programs and/or code segments, or other data to instruct the controller 302, and possibly other components of the touchscreen fuel panel 300, to perform the functionality described herein. Thus, the memory 306 can store data, such as a program of instructions for operating the touchscreen fuel panel 300, including its components (e.g., touchscreen display 304, controller 302, interface device 308, etc.), and so forth. It should be noted that while a single memory 306 is described, a wide variety of types and combinations of memory (e.g., tangible, non-transitory memory) can be employed. The memory 306 can be integral with the controller 302, can comprise stand-alone memory, or can be a combination of both. Some examples of the memory 306 can include removable and non-removable memory components, such as random-access memory (RAM), read-only memory (ROM), flash memory (e.g., a secure digital (SD) memory card, a mini-SD memory card, and/or a micro-SD memory card), solid-state drive (SSD) memory, magnetic memory, optical memory, universal serial bus (USB) memory devices, hard disk memory, external memory, and so forth.

The interface device 308 can be operatively configured to communicate with components of the touchscreen fuel panel 300. For example, the interface device 308 can be configured to retrieve data from fuel sensors, pumps, valves, actuators, other aircraft sensors and/or actuators, the flight management system, and/or any other aircraft controllers or data sources, transmit data for storage in the memory 306, retrieve data from storage in the memory 306, and so forth. The interface device 308 can also be communicatively coupled with the controller 302 to facilitate data transfer between components of the touchscreen fuel panel 300 and the controller 302. It should be noted that while the interface device 308 is described as a component of the touchscreen fuel panel 300, one or more components of the interface device 308 can be implemented as external components communicatively coupled to the touchscreen fuel panel 300 via a wired and/or wireless connection. The touchscreen fuel panel 300 can also include and/or connect to one or more input/output (I/O) devices (e.g., via the interface device 308), such as the touchscreen 304, another input device (e.g., a mouse, a trackball, a trackpad, a joystick, a line select device, a touchpad, a keyboard, a keypad, a microphone (e.g., for voice commands), etc.), another output device (e.g., a speaker, a display, a status light, etc.), and so forth. In embodiments, the interface device 308 includes or is coupled to a transmitter, receiver, transceiver, physical connection interface, or any combination thereof.

In at least one embodiment, the controller 302 may be configured to present requested information such as pump status, fuel status, valve status, engine manifold status, etc., and/or generate a control signal for at least one fuel system component via the interface device 308 in response to receiving a user input representing a user interaction with the touchscreen 304.

Figure 4A:
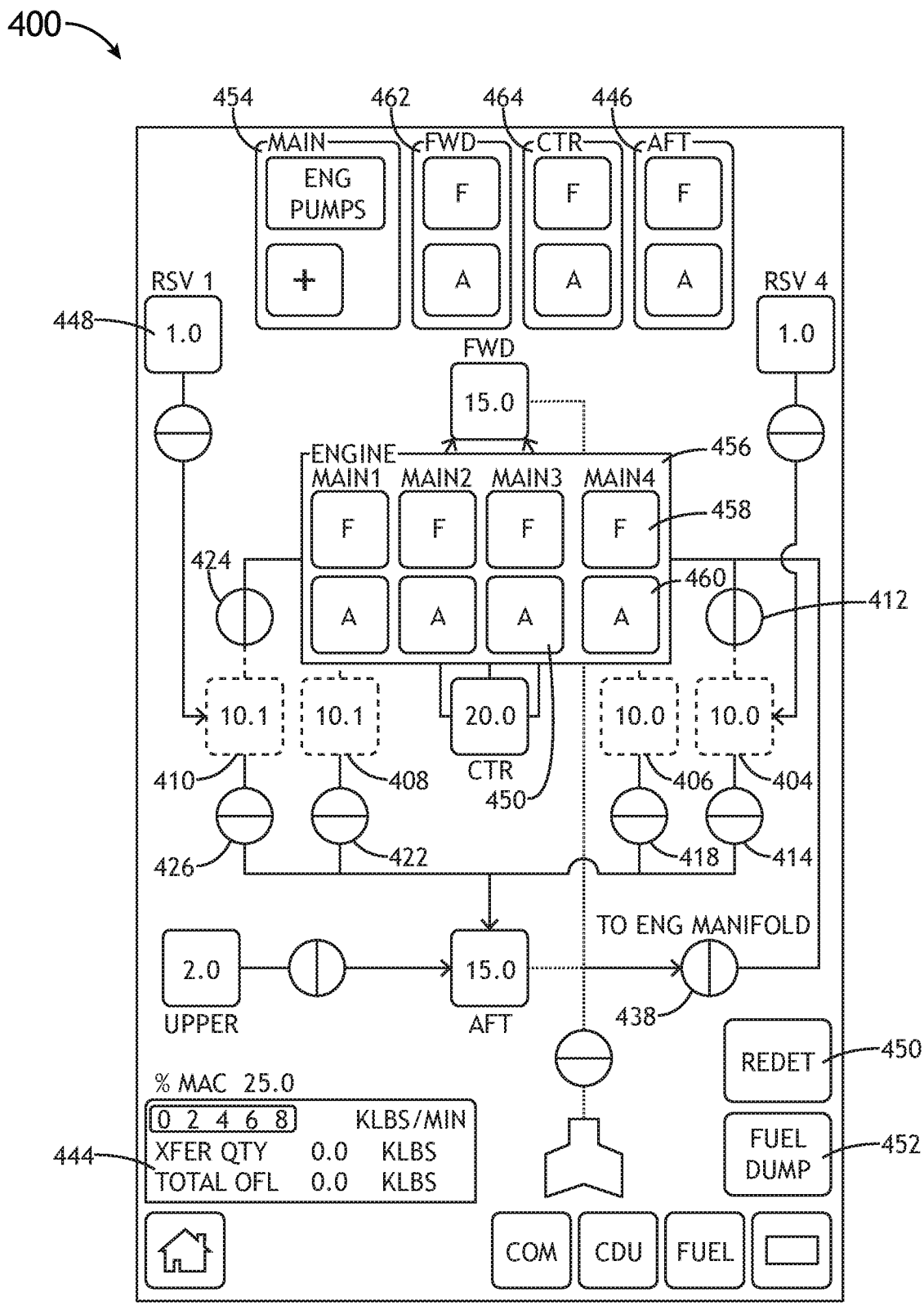
FIG. 4A shows a screen displayed by a touch screen fuel panel during a sequence according to an exemplary embodiment.
Figure 4B:
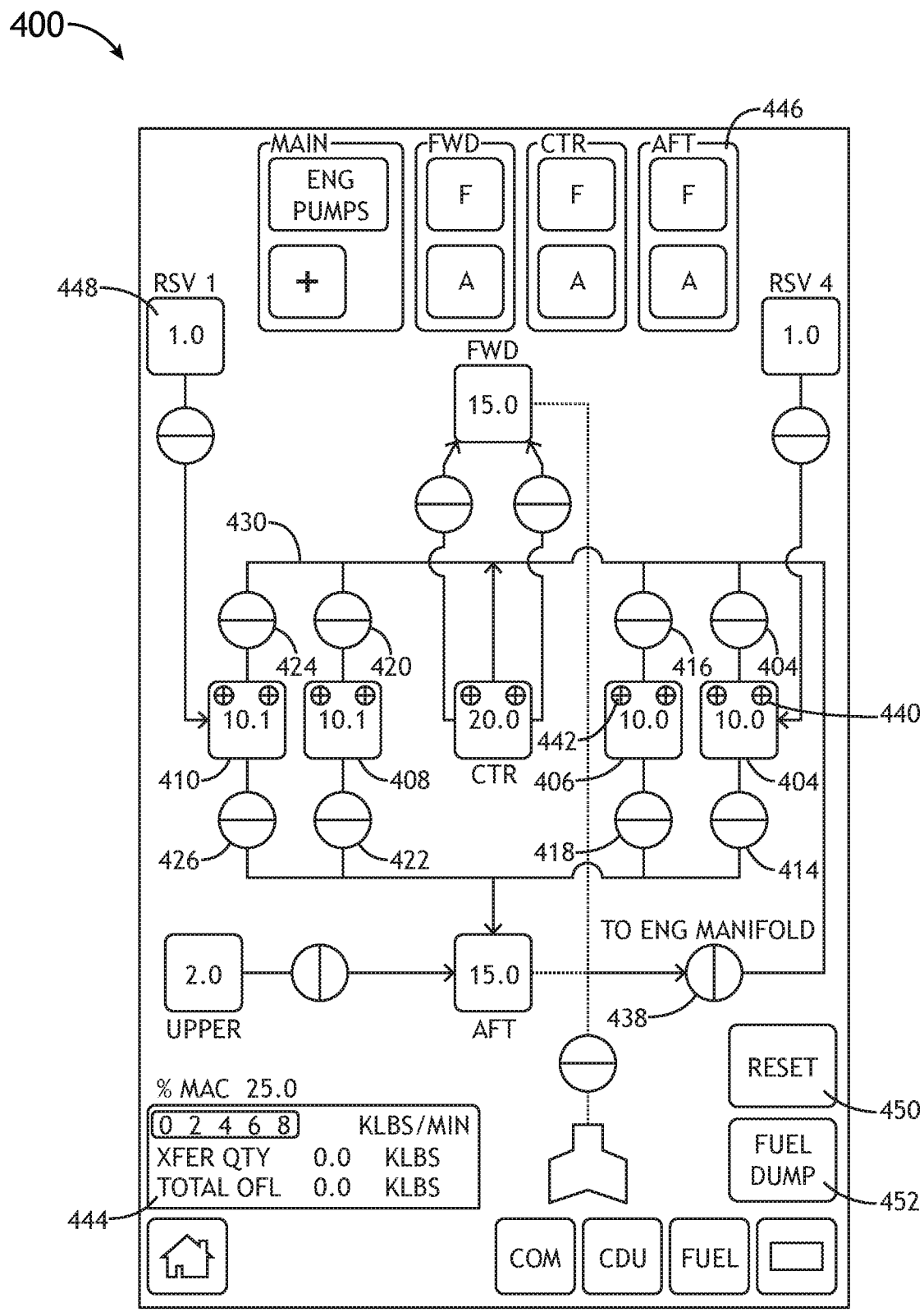
FIG. 4B shows a screen displayed by a touch screen fuel panel during a sequence according to an exemplary embodiment.

Referring to FIGS. 4A and 4B, screens 400 displayed by a touch screen fuel panel according to an exemplary embodiment are shown. The touchscreen fuel panel described herein provides status feedback for manifold, pump, and valve control which can be automated and result in status summary for operators (e.g., pilots or other flight crew). For example, pump, valve, fuel quantity, and probe accuracy may be checked prior to takeoff and periodically during a flight. The graphical user interface (GUI) presented by the touchscreen fuel panel adds situational awareness and provides flight crew with fuel system status information. Furthermore, a centralized, computerized, GUI based system allows for automation of complex tasks with a graphical representation of the step-by-step execution of those tasks.

In at least one embodiment, a schematic representation of a fuel system manifold is highlighted or recolored to represent fuel operation. For example, the schematic representation of the manifold may be highlighted or recolored with a first color (such as green) when refueling, a second color (such as blue) when draining, and a third color (such as magenta) when fuel is being directed to the engine.

In at least one embodiment, the GUI includes pump menus 446, 454, 462, 464 (e.g. Boost Pump Menu), system valves 412, 414, 416, 418, 420, 422, 424, 426, 438, pump status indications 440, 442 (e.g., Pump Status icons, animations, highlighting, and/or color indications), fuel quantity indications for each fuel reservoir 404, 406, 408, 410, 448 (e.g., fuel quantity indications associated with schematic representations of the fuel reservoirs), and fuel calculations 444 (e.g., transfer fuel quantity, total fuel quantity, etc.). Selecting system valves 412, 414, 416, 418, 420, 422, 424, 426, 438 causes a controller to generate signals to actuate a correspond valve or set of valves if selected system valve 412, 414, 416, 418, 420, 422, 424, 426, 438 represents a composite of multiple valves. Alternatively, a system valve 412, 414, 416, 418, 420, 422, 424, 426, 438, when selected, may cause the controller to present a sub-menu via the GUI with control options for the associated valve or set of valves. Furthermore, such functionality may be combined; for example, a simple tap may actuate the corresponding valves while a press-and-hold event may generate a valve option menu.

The GUI may further include additional features, such as a transfer quantity reset button 450, a fuel dump button 452 which may be guarded with specific access requirements such as a password/passkey, user authentication, or multi-factor authentication, or any other status/control icon, button, or text box that is selectable and/or configured to display status information. In at least one embodiment, a crew member may interact with various components of the fuel system, including additional functions of those components such as through fuel pump boost menus 446, 462, 464. Furthermore, the screen 400 may receive and display real-time status information pertaining to those components and other components that may not be directly addressable such as fuel lines 430 and fuel calculations 444. For example, during normal operations, a processor may update, in real-time, a graphical depiction of one or more system valves 412, 414, 416, 418, 420, 422, 424, 426 may be transitioned from a closed state to an open state; fore fuel pumps 440 and aft fuel pumps 442 may be animated to depict when such fuel pumps 440, 442 are actually operating. The GUI displays fuel status (such as amounts or limits) for individual fuel reservoirs 404, 406, 408, 410, 448. For example, the controller may be configured to receive reservoir control instructions (e.g., refueling, draining, offloading instructions, etc.) based on user selection of the schematic representation associated with a respective fuel reservoirs 404, 406, 408, 410, 448, whereby a sub-menu can be provided for the user, and the user may enter an instruction (such as drain limit, fill limit, etc.) for the selected fuel tank. The controller can then generate control signals to fulfill the user instruction.

In at least one embodiment, components in operation are rendered with a visual indication. For example, fuel reservoirs 404, 406, 408, 410 may be rendered in a different color while the corresponding fuel pumps are operating. Furthermore, fuel lines 428, 430 may be rendered in a different color corresponding to fuel functions within the manifold. In at least one embodiment, the fuel lines 430 may also be rendered with a graphical representation of fuel flow; for example, with moving or animated dashed lines to indicate a flow direction. Likewise, the speed of such moving dashed line may correspond to a flow rate. Fuel flow through particular system valves 412, 414, 416, 418, 420, 422, 424, 426 may be indicated by extending the graphical representation of the fuel lines 428, 430 to the implicated system valve 412, 414, 416, 418, 420, 422, 424, 426, including color delineations of the fuel functions.

In at least one embodiment, complex or composite tasks that require sequential operation of various components 412, 414, 416, 418, 420, 422, 424, 426, 438, 440, 442, 446, 462, 464 may be programed, or a stored procedure retrieved, and executed via a controller which also graphically depicts the execution of each task and any feedback corresponding to those tasks in real-time. Components 412, 414, 416, 418, 420, 422, 424, 426, 438, 440, 442, 446, 462, 464 may be rendered in distinct colors to indicate success or failure of a particular task. Furthermore, components 412, 414, 416, 418, 420, 422, 424, 426, 438, 440, 442, 446, 462, 464 may be rendered in a color or style indicative of routine or periodic component failure based on historical task execution status.

In at least one embodiment, one or more components 412, 414, 416, 418, 420, 422, 424, 426, 438, 440, 442, 446, 462, 464 may represent assemblies of sub-components (such as an engine pump widget 456 activated via a main engine pump element 454). The engine pump widget 456 displays individual engine pump elements 458, 460 for each fore and aft pump associated with each engine. In at least one embodiment, each individual engine pump element 458, 460 is individually addressable to start the corresponding engine pump. Each individual engine pump element 458, 460 may also indicate through color differentiation a current state of the corresponding pump; for example, blue when inactive, yellow during a startup process, green when active, and red if a fault is detected. In at least one embodiment, the main engine pump element 454 may have multiple functionalities;

for example, simply selecting the main engine pump element 454 initiates the engine pump widget 456 while a tap-and-hold event may send signals to activate all of the engine boost pumps without initiating the engine pump widget 456.

In at least one embodiment, the GUI includes individually selectable fuel pump boost menus 446, 462, 464 for controlling forward, center, and aft pumps of the fuel management system. Selecting any of the fuel pump boost menus 446, 462, 464 generates one or more signals to turn the corresponding pump/pumps associated with the selected fuel pump boost menu 446, 462, 464. In at least one embodiment, selecting one of the fuel pump boost menus 446, 462, 464 initiates a widget or sub menu to present control options for the individual pump/pumps associated with the selected fuel pump boost menu 446, 462, 464. In at least one embodiment, pump status is represented by an animation such as a rotating element.

Where any sub-component is active, the graphical representation of the corresponding components 412, 414, 416, 418, 420, 422, 424, 426, 438, 440, 442, 446, 462, 464 may indicate such activity. Selecting the corresponding component 412, 414, 416, 418, 420, 422, 424, 426, 438, 440, 442, 446, 462, 464 may cause the controller to render a graphical representation of the assemblage of sub-components and allow individual sub-components to be interacted with, or status information corresponding to individual sub-components.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
at least one processor;
an avionics system interface in data communication with the processor;
a touchscreen display connected to the processor; and
a memory in data communication with the processor storing processor executable code for configuring the at least one processor to:
establish a data connection with one or more components in an avionics fuel system;
generate a graphical user interface at the touchscreen display of the one or more components, the graphical user interface including a boost pump menu with at least one selectable icon for a set of engine boost pumps and a plurality of individually selectable icons for forward, center, and aft boost pumps;
receive real-time status information for each of one or more components via the avionics system interface;
render the real-time status information via an animation of the one or more components;
generate one or more control signals for the set of engine boost pumps based on a user input; and
render graphical representations of two or more fuel flows, each comprising a distinct color corresponding to a fuel function within a manifold.

2. The computer apparatus of claim 1, wherein the processor executable code further configures the at least one processor to:
receive a plurality of inputs corresponding to a composite task;
store the plurality of inputs; and
sequentially apply the plurality of inputs.

3. The computer apparatus of claim 1, wherein the processor executable code further configures the at least one processor to:
receive an input corresponding to a graphical representation of an assemblage of individually addressable sub-components;
render an expanded view of each of the individually addressable sub-components;
determine that any individually addressable sub-component has a fault; and
render the graphical representation of the assemblage in a color indicate a fault.

4. The computer apparatus of claim 3, wherein the processor executable code further configures the at least one processor to:
receive real-time status information corresponding to each of the individually addressable sub-components; and
render a graphical representation of the real-time status information of each of the individually addressable sub-components.

5. The computer apparatus of claim 1, wherein the processor executable code further configures the at least one processor to:
determine that the real-time status information corresponds to system fault; and
render a graphical representation of a component corresponding to the system fault in a distinct color.

6. The computer apparatus of claim 1, wherein the processor executable code further configures the at least one processor to automatically store an output of touchscreen inputs.

7. An aircraft fuel management system comprising:
at least one processor;
an avionics system interface in data communication with the processor;
a touchscreen display connected to the processor; and
a memory in data communication with the processor storing processor executable code for configuring the at least one processor to:
establish a data connection with one or more components in an avionics fuel system;
generate a graphical user interface at the touchscreen display of the one or more components, the graphical user interface including a boost pump menu with at least one selectable icon for a set of engine boost pumps and a plurality of individually selectable icons for forward, center, and aft boost pumps;
receive real-time status information for each of one or more components via the avionics system interface;
render the real-time status information via an animation of the one or more components;
generate one or more control signals for the set of engine boost pumps based on a user input; and
render graphical representations of two or more fuel flows, each comprising a distinct color corresponding to a fuel function within a manifold.

8. The aircraft fuel management system of claim 7, wherein the processor executable code further configures the at least one processor to:
- receive an input corresponding to a graphical representation of an assemblage of individually addressable sub-components;
- render an expanded view of each of the individually addressable sub-components;
- determine that any individually addressable sub-component has a fault; and
- render the graphical representation of the assemblage in a color indicate a fault.

9. The aircraft fuel management system of claim 8, wherein the processor executable code further configures the at least one processor to:
- receive real-time status information corresponding to each of the individually addressable sub-components; and
- render a graphical representation of the real-time status information of each of the individually addressable sub-components.

10. The aircraft fuel management system of claim 7, wherein the processor executable code further configures the at least one processor to:
- determine that the real-time status information corresponds to system fault; and
- render a graphical representation of a component corresponding to the system fault in a distinct color.

11. The aircraft fuel management system of claim 7, wherein the processor executable code further configures the at least one processor to automatically store an output of touchscreen inputs.

* * * * *